United States Patent

Berger et al.

Patent Number: 5,949,237
Date of Patent: Sep. 7, 1999

[54] MICROWAVE CAVITY RESONATOR FOR CONTINUOUS SPECTROSCOPIC GAS ANALYSIS

[75] Inventors: Lutz Berger, Eggenstein-Leopoldshafen, Germany; Franz Königer, Buhl, France; Hans-Dieter Metzger, Karlsruhe; Gerhard Schmitt, Frankfurt, both of Germany

[73] Assignee: Forschungszentrum Karlsruhe GmbH, Karlsruhe, Germany

[21] Appl. No.: 09/115,729

[22] Filed: Jul. 15, 1998

Related U.S. Application Data

[63] Continuation-in-part of application No. PCT/EP97/00175, Jan. 16, 1997.

[30] Foreign Application Priority Data

Feb. 3, 1996 [DE] Germany ............... 196 03 905

[51] Int. Cl.⁶ ..................................... G01N 22/00
[52] U.S. Cl. ...................... 324/636; 324/634; 73/23.2
[58] Field of Search ........................ 324/634, 636; 73/23.2; 333/227, 230, 231, 232

[56] References Cited

U.S. PATENT DOCUMENTS

| | | | |
|---|---|---|---|
| 3,973,186 | 8/1976 | Uehara et al. | 324/636 |
| 4,894,603 | 1/1990 | Berger et al. | 324/636 |
| 4,973,699 | 11/1990 | Berger et al. | 73/23.2 |
| 5,548,217 | 8/1996 | Gibson et al. | 324/636 |

FOREIGN PATENT DOCUMENTS

| | | |
|---|---|---|
| 37 23 606 | 1/1989 | Germany . |
| 36 45 240 | 8/1993 | Germany . |

OTHER PUBLICATIONS

D. Dortmann et al., "Die Mikrowellenspektroskopie, ein neues System fur die Bestimmung von Ammoniak in Rauchgasen", *VGB Kraftwerkstechnik*, vol. 72, nr. 1, Jan. 1992, pp. 65–69.

Paulus, "Selektives Messen in der Prozessanalytik mit dem Mikrowellenprozessanalysator Mipan", *Technisches Messen TM*, vol. 58, nr. 11, Nov. 1, 1991, pp. 433–438.

*Primary Examiner*—Diep Do
*Attorney, Agent, or Firm*—Klaus J. Bach

[57] ABSTRACT

In a microwave resonator for continuous spectroscopic gas analysis with a microwave cavity having dimensions depending on the operating frequency and a setting for a low quality Q of its base mode and microwave reflectors disposed at its opposite ends and including a round hollow conductor part and a co-axial conductor part separated by a pressure-tight dielectric window, an internal conductor part is axially movably supported in the coaxial conductor part by the microwave reflector at one end of the co-axial conductor part, the other reflector being axially movable for tuning the resonator to a maximal absorption frequency and a by-pass line extends past the co-axial conductor part in the area of the dielectric window and has a short branch connected to the co-axial conductor part and including a restrictor for supplying only a relatively small flow of gas from the bypass line to the conductor part of the microwave resonator.

7 Claims, 3 Drawing Sheets

MICROWAVE CAVITY RESONATOR FOR CONTINUOUS SPECTROSCOPIC GAS ANALYSIS

This is a Continuation-in-Part application of international application PCT/EP97/00175 filed Jan. 16, 1997 and claiming the priority of German application No. 196 03 905.3 filed Feb. 3, 1996.

BACKGROUND OF THE INVENTION

The invention relates to a microwave cavity resonator for use as a measuring cell for process gas analyzers. With such a device, the concentration of a predetermined gas component in a process gas is determined by microwave spectroscopic methods utilizing the Stark effect. Usually, the measurements are performed according to the penetration radiation principle, wherein spatially very long measuring cells are used (see DE 36 45 240 C2) in order to obtain a high detection sensitivity.

If such large lengths are to be avoided, resonators can be used as an alternative. In order to be able to detect very low gas concentrations in a highly sensitive way, the Q-factor of the resonator should be high. However, a high Q-factor, that is, a high sensitivity of the resonator also causes the resonator to be sensitive to ambient influences. These influences must be neutralized by stabilizing measures (see in this respect R. Reinschlüssel, et al., "Design of a Sensitive Cavity . . . , in AEU, volume 40, 1986, issue No.5, pages 313–320). The compensation for the external influences results in additional construction expenses which substantially increases building costs.

An operative gas analyzer is presented in DE-Z: Technisches Messen 58(1991) 11, pages 433 to 438. Herein a microwave process analyzer for the rapid analysis of for example exhaust gases is described.

U.S. Pat. No. 3,973,186 discloses a microwave hollow resonator for continuous spectroscopic gas analysis. The resonator has a rectangular shape but it may also be cylindrical. The resonance frequency of the resonator can be changed so that various polar molecules can be individually examined.

The object of the invention is derived from the fields of power generation and waste combustion, where the concentrations of ammonia in the exhaust gas should be determined on a real-time basis and without sensitivity to other compounds of the process; that is, the exhaust gases. For this purposes, a analysis apparatus capable of withstanding the environment must be installed in the exhaust gas discharge system which senses the concentration of the particular gas content or gas components reliably over a long period of operation.

SUMMARY OF THE INVENTION

In a microwave resonator for continuous spectroscopic gas analysis with a microwave cavity having dimensions depending on the operating frequency and a setting for a low Q factor of its base mode and microwave reflectors disposed at its opposite ends and including a round hollow conductor part and a co-axial conductor part separated by a pressure-tight dielectric window, an inner conductor part is axially movably supported in the coaxial conductor part by the microwave reflector at one end of the co-axial conductor part, the other reflector being axially movable for tuning the resonator to a maximal absorption frequency and a by-pass line extends past the co-axial conductor part in the area of the dielectric window and has a short branch connected to the co-axial conductor part and including a restrictor for supplying only a relatively small flow of gas from the bypass line to the conductor part of the microwave resonator.

The basic idea of the invention resides in the reduction of the length of the measuring cell by a resonator having a lower Q-factor (Low-Q-Resonator). This resonator is tuned to the absorption frequency of the measuring gas, that is, the component in the process gas to be measured. The microwave characteristics essentially determine its geometry. By multiple reflection in the resonator the effective travel length within the resonator is substantially greater than its geometric length. As a result, a spatially substantially smaller resonator size is possible. The resonator is divided by a dielectric window, in a pressure and gas tight manner, into two chambers, a round hole conductor part and a coaxial conductor part.

The free pointed end of the inner conductor within the coaxial conductor part is disposed immediately before the dielectric window, that is at a small distance therefrom, which is only large enough to permit an axial displacement for an adjustment and fine-tuning of the microwave state. The length of the inner conductor, that is a Stark electrode, in the measuring cell must be so adjustable, that its tip is disposed at a nodal point of the electric field.

The co-axial conductor part of the resonator forms the actual measuring cell of the interaction space. The process gas volume, which is directed from the by-pass line is continuously fed into the measuring cell adjacent the dielectric window and is suctioned off from there, by way of gas passages in the microwave reflector firmly disposed therein, in a continuous flow with the largest possible flow cross-section whereby a predetermined pressure drop is established in the measuring cell.

In the round hollow conductor part of the resonator, the microwave in-and out coupling occurs. There, the microwave reflector is axially adjustable for providing optimal resonance conditions and optimal in- and outcoupling conditions.

The resonator may be provided specifically for measuring a particular type of gas wherein its resonator geometry is tuned only to the particular type of gas. But it may also be provided for other types of gases whose absorption lines are in a similar wave length range. It would then be advantageous to over-dimension the resonator. For reliable measurements, the operating parameters would be so selected that only one resonance frequency occurs in a given frequency range.

In order to avoid external influences such as mechanical effects on the resonator and to substantially avoid the effects of outer temperature changes the resonator has a thick wall with a high heat capacity. A measuring device in which such a resonator and the measuring cell are spatially separated from other resonator areas and whose measuring quality is about between 1000 and 2000 (Low Q Resonator) is suitable for a rough process environment and fulfills the expectations for detection sensitivity, ease of servicing, stability and economical design.

An embodiment of the low Q-factor microwave hollow space resonator for the detection or, respectively, the determination of the concentration of specifically ammonia in exhaust gas is schematically shown in the drawings and will be described below in greater detail.

DESCRIPTION OF A PREFERRED EMBODIMENT

Figure 1A:
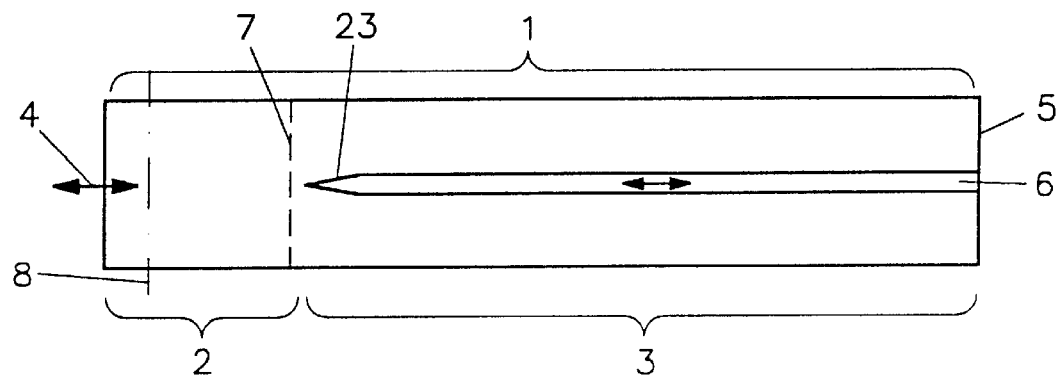
FIG. 1a shows a resonator with its round hole and coaxial conductor part.

The design of the Low-Q-Resonator 1 is simple and comprises in principle for individual components (FIG. 1b):

1. The coaxial conductor part 3, that is, the actual measuring cell 3 comprising essentially an inner conductor 6 forming a Stark septum or Stark electrode 6, which is supported co-axially by a penetration in the stationary microwave reflector 5 and by a Teflon star support member 10 disposed adjacent the tip 23 of the conductor 6. The Teflon star 10 is so shaped that it leaves the microwave in the resonator 1 and the continuos measuring gas flow essentially unaffected.

2. The round hollow conductor part 2 forming a microwave coupling block with in-and-out coupler 8 and the microwave reflector 4 in the form of a $\lambda/4$ transformer, which is axially movable and makes two tuning functions possible:

a) for the resonance tuning in the resonator 1 and, b) for the setting of the optimal in-and-out-coupling of the microwave.

1. 3. The co-axial conductor part 3, which represents the actual measuring cell 3 with a diaphragm or restriction 9 for the measuring gas inlet from the process gas of the by-pass line 21 (FIG. 3) and the stationary microwave reflector 5, which is designed as a mode filter and serves at the same time as a support and penetration for the axially movable inner conductor 6, that is, the Stark electrode or Stark septum. The measuring gas is suctioned off continuously by way of bores in the microwave reflector 5 and affects the microwave reflection very little or not at all.

2. 4. The dielectric window 7 in the form of a Kapton foil, which separates the round hole conductor part 2 from the coaxial conductor part 3 of the resonator 1. The foil 7 is mechanically sufficiently tough and chemically sufficiently inert so that the pressure difference between the two resonator chambers 2, 3 can be maintained and no chemical reactions occur. In the round hollow conductor part 2, there is generally ambient pressure whereas a vacuum pressure is maintained in the coaxial conductor part 3. The foil has essentially no effect on the microwave in the resonator 1.

For the dimensioning of the resonator 1 several modes of H- and E- type waves in the frequency range of interest are taken into consideration. The base mode is the wave type with the highest ratio of cut-off-wave length to the diameter of the resonator 1. In the example, this is the $H_{11}$ mode. The establishment of the Low-Q-resonator 1 is based on the $H_{11}$-mode. All other wave types have at this point a cut-off-frequency which is far above the desired frequency range so that they cannot propagate in the resonator 1.

On the basis of known high frequency technical or microwave technical considerations (see for example, Meinke Gundlach, "Taschenbuch der Hf Technik") the inner diameter of the resonator 1 is selected to be D=10 mm for manufacturing reasons. With small design changes the resonator 1 can then be used for frequencies up to about 30 GHz since the limit frequency $\lambda_0$ is lower, that is, for the $H_{11}$ mode, it is about 17.56 GHz.

Generally, the wave length in a hollow conductor $\lambda_g$ with the wave length in a free space $\lambda_o$=12.556 mm ($f_o$=23.87013 GHz) and the cut-off-wave-length $\lambda_c$ of the wave guide is calculated in accordance with the equation:

$$\lambda_g = \lambda_0/\sqrt{[1-(\lambda_0/\lambda_c)^2]}$$

For an adaptation to the $H_{11}$-mode in the round hole 2 and the co-axial conductor 3, with the diameter D=10 mm, the diameter d of the inner conductor 6 that is the Stark electrode 6 must be adapted to by adaptation of the cut-off-wave length ($\lambda_{cHL}$(in the round hollow conductor)=$\lambda_{cKoax}$ (in the coaxial hollow conductor)=18.54 mm). For diameter ratios D/d smaller than 5, the following equations are valid:

$$\lambda_c = 0.973 \times \pi/2 \times (D+d)$$

$$d = \lambda_c/0.973 \times 2/\pi - D$$

From this, an optimal diameter of d=2.13 mm is calculated for the Stark electrode. With commercially available rod material (stainless steel, brass) of 2 mm, a sufficient adaptation of the electromagnetic waves in the hollow conductor to the co-axial conductor part 3 ($\lambda_{ckoax}$=18.34 mm) is achieved. Material of such a thickness also attenuates mechanical vibrations of the Stark electrode which may occur in the process. Such vibrations must be avoided because they modulate the Stark voltage and, consequently, the signal amplitude which is undesirable.

For the various values of the parameter p, of the integer multiple of half the wave length, with the $H_{11}$-mode ($\lambda_c$=1.706×D) at a resonance frequency $f_o$=23.87013 GHz ($\lambda_o$=12.556 mm, $\lambda_{gHL}$=18.54 mm, the resultant wave length in the round hollow conductor 2) for the desired absorption line of the ammonia ($HH_3$) and for D=10 mm the following approximation values for the length L' of the resonator part 2 without the co-axial conductor part 3 (FIG. 1a+b) are obtained:

| P | 4 | 5 | 6 | 7 | 8 |
|---|---|---|---|---|---|
| L'/mm | 37.09 | 46.36 | 55.63 | 64.89 | 74.16 |

For the co-axial conductor part 3 of the low-Q-Resonator 1, the following is obtained in the same way

| P | 25 | 26 | 27 | 28 | 29 |
|---|---|---|---|---|---|
| L/mm | 201.00 | 209.04 | 217.08 | 225.12 | 225.12 |

The length L of the Stark electrode 6 was measured for an optimal resonance representation at about 207 mm or 215 mm, respectively, for subsequent similar states in the resonator 1. The distances between two optimal states, that is, half a hollow conductor wave length in the co-axial part of the resonator 1 is consequently about 8 mm. For the same cut-off wave length $\lambda_c$ of 18.4 mm, the distance between two half hollow conductor wave lengths in the non-coaxial part 2 of the round hollow conductor is 9.3 mm. The co-axial conductor part 3 of the resonator 1 is therefore about 207 mm, the round hollow conductor part 2 is about 55 mm long.

The half value width of the resonator performance line 13 of the resonator 1 (FIG.2) is preferably greater than the half value width of the absorption line 14 by a factor of about 2 to 3. The absorption line for $NH_3$ is about 7 MHz at the given pressure (FIG. 2), but is smaller at lower pressure and increases with higher pressures (line widening). With these data first a Q-factor of the resonator 1 of 1000 to 2000 is sought. The configuration of the Low-Q-resonator 1 in accordance with the considerations given above leads finally to a Q-factor of about 1200.

The microwave supply from the sender 15 occurs by way of a rectangular hollow conductor 11 and a coupling slot in the wall of hollow round conductor 2. The detector 17 is connected in the same way. The two coupling slots each have a length of about half the resonance wave length. The width and the wall thickness are small as compared to the slot length. From a microwave point of view, the wall thickness in the in- and outcoupling slot area should be infinitely small. It is actually only so small that there is still sufficient mechanical stability during operation. It is small enough however, that the influence on the microwave is negligable.

Figure 1B:
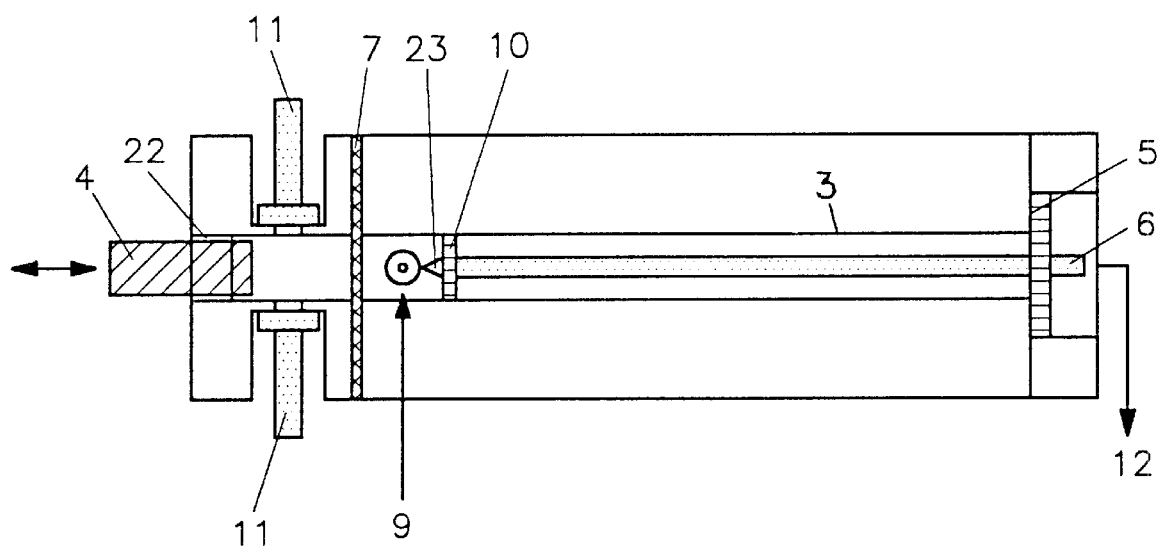
FIG. 1b is a schematic representation showing the design of the Low-Q-Resonator.

Coupling to the process is achieved in accordance with the schematic drawing of FIG. 1b by way of the by-pass line 21, which is generally heated and which conducts a part of gas flow to be surveyed past the measuring cell 3. A nozzle extending from the diaphragm 9 reaches into the main flow in the by-pass line 21 and diverts continuously the predetermined measuring gas volume. The diaphragm 9, which may also be a valve or another restriction reduces the pressure in the measuring cell 3 by extracting the gas to be measured therefrom so that the intended pressure drop between the diaphragm and the microwave reflector 5 at the other end of the measuring cell 3 is maintained. The suction power of the pump 20 is therefore adapted to the pressure range which may be different with other gases to be measured.

The low-Q-measuring system optimized for a rapid detection of measurement values requires several additional measures in the conception of the gas passage. It is important that the by-pass line 21 is arranged as closely as possible to the measuring cell 3 so that there is no excess volume between the diaphragm 9 in the measuring cell 3 and the intake for the gas to be measured, that is, the nozzle inlet in the area of the highest gas flow in the by-pass line 21. The adjustable diaphragm 9 replaces a valve which is generally quite complex.

If the pressure gradient in the measuring cell is excessively high, the signal strength is reduced because the measuring signal is dependent on the pressure. For a measuring system which is optimized as far as speed is concerned, a compromise must be made between signal amplitude, gas flow and pressure in the cell.

Figure 2:
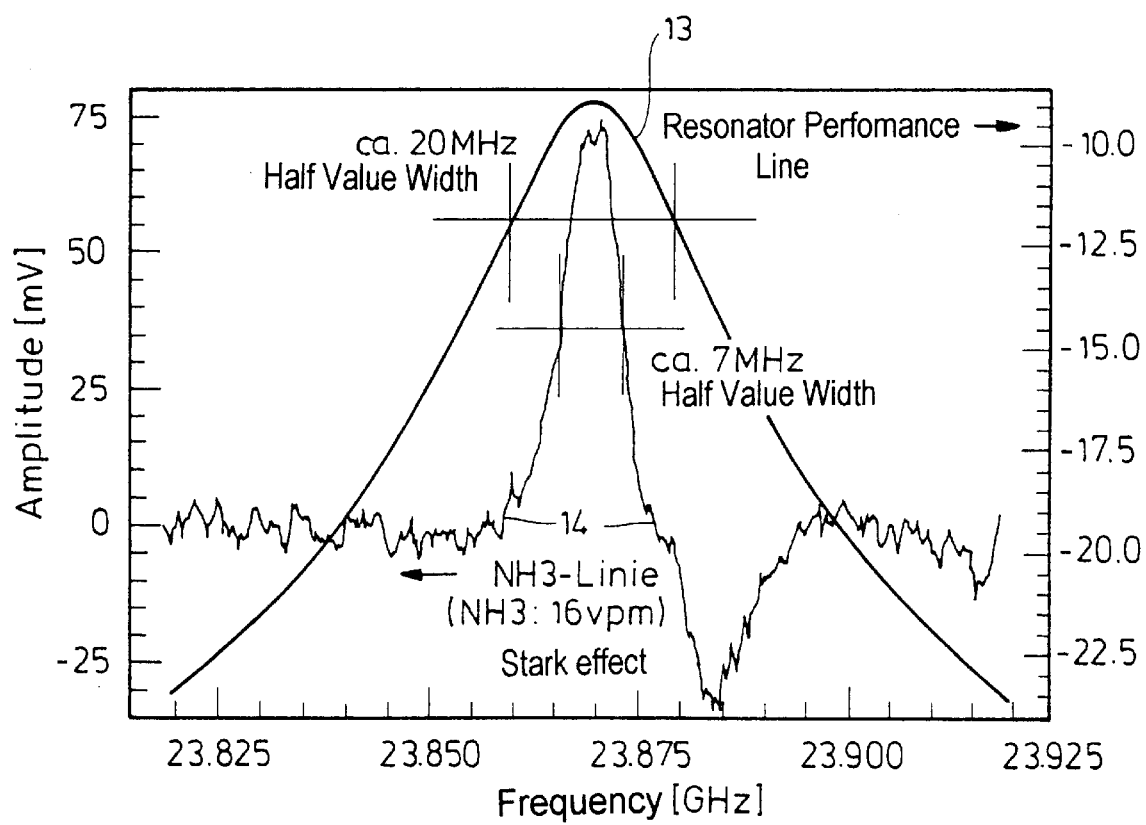
FIG. 2 shows a comparison of the resonator half-value width with the line width of an $NH_3$ line.
Figure 3:
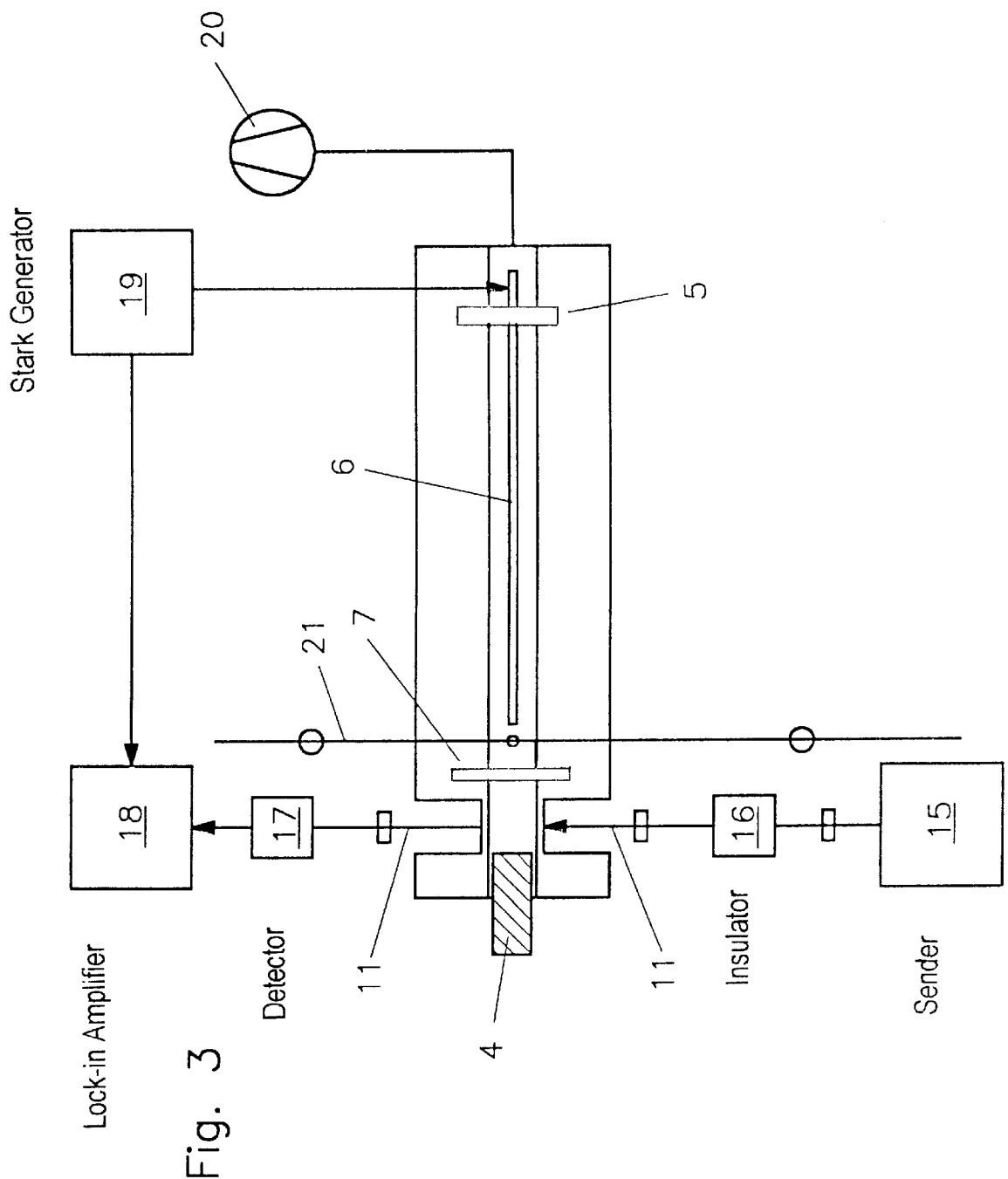
FIG. 3 shows schematically the basic measuring arrangement of the gas analyzer.

The whole design of the gas analyzer is based on the same scheme as it is used in DE 36 454 240 C2 and shown in FIG. 3. The frequency-stabilized microwave sender 15, that is a Gunndiode, radiates into the low Q resonator 1. The sender 15 is uncoupled from the in-coupling area by an isolator 16. The microwave field modulated by the Stark generator 19 is recorded by the detector 17 and supplied to the lock-in amplifier 18. The amplifier 18 amplifies the received signal phase-synchronously with the Stark generator signal to such an extent that the evaluation unit, for example, a microprocessor, can make the processed signal available. FIG. 2 shows that the line displaced by the Stark effect is sufficiently modulated so that the actual absorption line 14 is symmetrical.

Because of the short gas exchange times,—about 100 measuring cell volumes/sec in the resonator 1, which is achieved by the small dimensions of the measuring cell and optimization of the gas flow passages—the response time to changes in the measuring gas is substantially shortened. For the pure measuring system without external additional sample drawing conduits, values of about 30 milliseconds are achieved with ammonia which is a compound with strong adsorption properties.

During normal measuring operation, response times of clearly less than one second are achieved. This means a response faster by at least the factor 200 as compared to the apparatus described in DE 36 45 240 C2 is achieved; for the detection limit, the improvement is by a factor of 2. The analyzer with the low-Q-factor measuring cell 1 reaches a measuring sensitivity using ammonia ($NH_3$) of 0.1 vppm with a time constant of the lock-in amplifier of 20 seconds. In this way, control tasks can now be accomplished which could not be solved in the past because of the long response time of the analyzers.

What is claimed is:

1. A microwave cavity resonator for continuous spectroscopic gas analysis to determine the concentration of a given compound in a process medium flow, said microwave resonator having a cavity with a diameter which depends on the operating frequency of the microwave resonator and other dimensions and a setting for a low Q-factor of the base mode of the microwave resonator with the highest ratio of cut-off wave length to the diameter of the resonator and further having a resonator performance line with a half value width set to a value which is greater than the half value width of an absorption line to be measured by a factor in the lower single digit range, said resonator being a hollow cylindrical body having microwave reflectors disposed at opposite ends of the microwave resonator and including a round hollow conductor part and a coaxial conductor part which are separated by a gas and pressure-tight dielectric window, an internal conductor disposed in said coaxial conductor part so as to be axially movable therein and forming an electrode for the application of a Stark modulation, said internal conductor extending through, and being supported by, the microwave reflector at one end of said coaxial conductor part, two hollow conductors attached to said round hollow conductor symmetrically with respect to the axis of said resonator, one of said microwave reflectors being stationary and the other being axially movable for tuning said resonator to a predetermined maximal absorption frequency and for a setting providing for optimal in- and out-coupling of the microwave, a bypass line extending past said coaxial conductor part adjacent said dielectric window and having a branch of short length extending to said coaxial conductor part and including a restrictor generating a pressure drop for supplying only a restricted continuous gas flow to said coaxial conductor part and means for removing gas from said coaxial conductor part through openings formed in the microwave reflector at the end of said coaxial conductor part.

2. A microwave cavity resonator according to claim 1, wherein said base mode is the $H_{11}$ mode.

3. A microwave cavity resonator according to claim 1, wherein said resonator has thick walls to provide for good mechanical stability and a high heat capacity.

4. A microwave cavity resonator according to claim 1, wherein the inner diameter of the hollow cylindrical resonator body is at least of a size as determined by the excitation of the predetermined mode.

5. A microwave cavity resonator according to claim 4, wherein said microwave reflector, which is stationary in said coaxial conductor part, acts as a mode filter and supports the Stark electrode and further includes openings through which the gas to be measured can be uniformly sucked out of the coaxial conductor part and wherein said microwave reflector in said round hollow conductor part acts as a $\lambda/4$ transformer and is separated from the resonator wall in an electrically conductive way by a thin-walled dielectric hollow cylinder.

6. A microwave cavity resonator according to claim 5, wherein said Stark electrode has a tip formed at its free end to provide for a transition between the round hollow conductor part and the coaxial conductor part, which transition is microwave shock-free, said electrode being supported coaxially by way of a dielectric star-like support member which does not essentially affect the gas flow.

7. A microwave cavity resonator according to claim 6, wherein said restriction is exchangeably and includes a nozzle-like projection extending into an area of said by-pass line with fast gas flow.

* * * * *